United States Patent [19]
Blades

[11] Patent Number: 6,114,700
[45] Date of Patent: Sep. 5, 2000

[54] NDIR INSTRUMENT

[75] Inventor: Frederick K. Blades, Boulder, Colo.

[73] Assignee: Anatel Corporation, Englewood, Colo.

[21] Appl. No.: 09/052,136

[22] Filed: Mar. 31, 1998

[51] Int. Cl.[7] ............................ G01N 21/35; G01N 21/61
[52] U.S. Cl. .................................................. 250/343
[58] Field of Search ............................................. 250/343

[56] References Cited

U.S. PATENT DOCUMENTS

| | | |
|---|---|---|
| 4,304,996 | 12/1981 | Blades . |
| 4,346,296 | 8/1982 | Passaro et al. . |
| 4,398,091 | 8/1983 | Passaro . |
| 4,687,934 | 8/1987 | Passaro et al. . |
| 4,950,900 | 8/1990 | Takeuchi et al. ........................ 250/346 |
| 5,464,982 | 11/1995 | Drucker et al. ........................... 250/343 |
| 5,528,039 | 6/1996 | Bernard ..................................... 250/343 |
| 5,625,189 | 4/1997 | McCaul et al. ........................... 250/343 |
| 5,886,348 | 3/1999 | Lessure et al. ...................... 250/339.13 |
| 5,905,270 | 5/1999 | McCaughey et al. ................... 250/573 |

FOREIGN PATENT DOCUMENTS

277124 A1   3/1990   Germany ................................ 250/343

OTHER PUBLICATIONS

Small et al, "Oxidation and detection techniques in TOC analysis", *American Laboratory*, Feb. 1986, pp. 141–150.

*Primary Examiner*—Constantine Hannaher
*Attorney, Agent, or Firm*—Michael de Angeli

[57] ABSTRACT

An improved NDIR instrument as used for measuring the carbon dioxide content of a gas sample includes an electrically modulated incandescent lamp disposed at one end of a sample cell for containing the gas to be analyzed, and a first pyroelectric detector at the other end of the cell. The intensity of modulated radiation incident on the detector is measured using paired dual-slope integrators, each integrating the signal on alternate half-cycles of the signal provided by the detector, to determine the concentration of infrared-absorptive gas in the cell. At intervals, the cell is purged by an infrared-transparent gas, and a similar measurement made, allowing correction for long-term drift in the optical characteristics of the instrument.

The instrument correctly determines the concentration of $CO_2$ despite "leakage" of the broad-band infrared radiation emitted by the lamp through the sample to be analyzed.

In a second embodiment, a second pyroelectric detector is juxtaposed to the lamp opposite the cell, and the intensity of the radiation emitted by the lamp controlled by a feedback loop including the second detector.

54 Claims, 4 Drawing Sheets

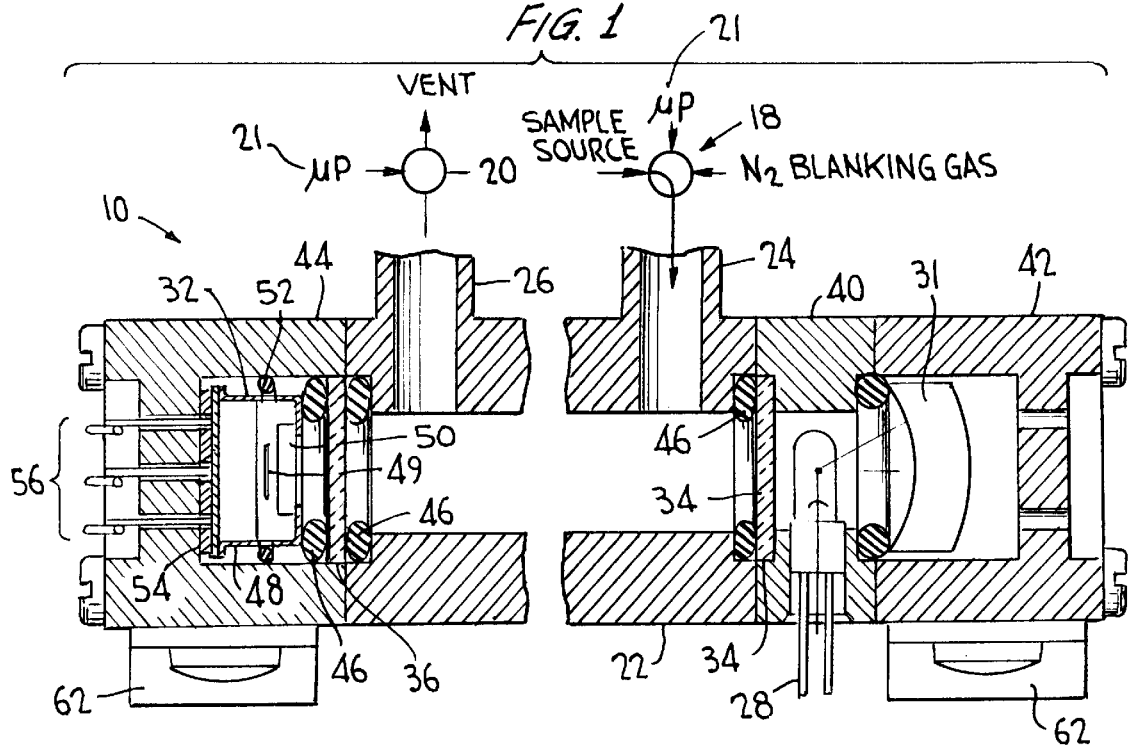
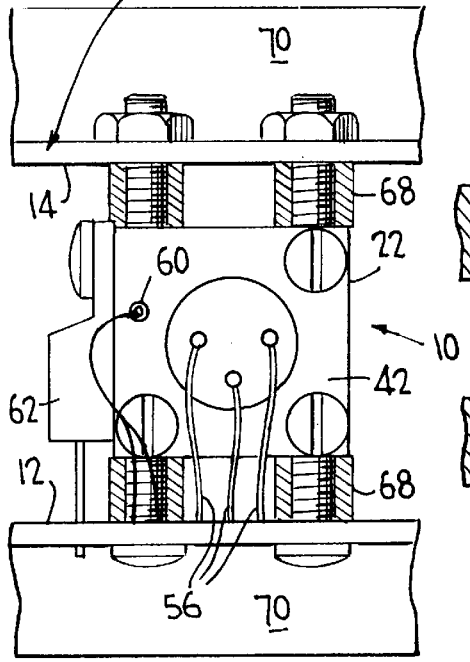
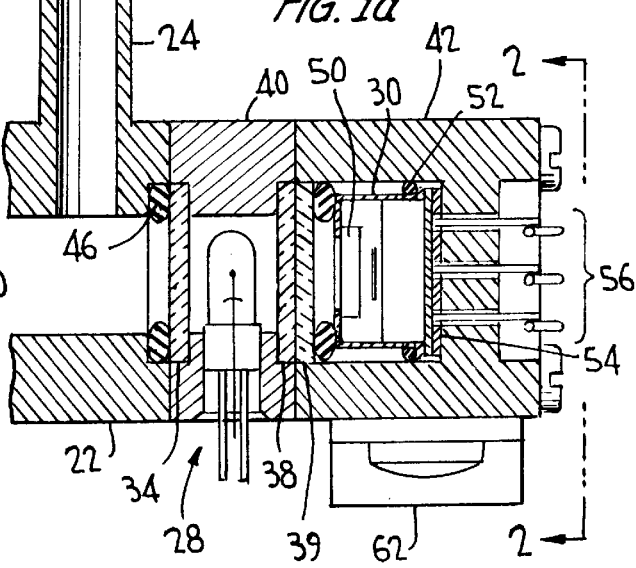

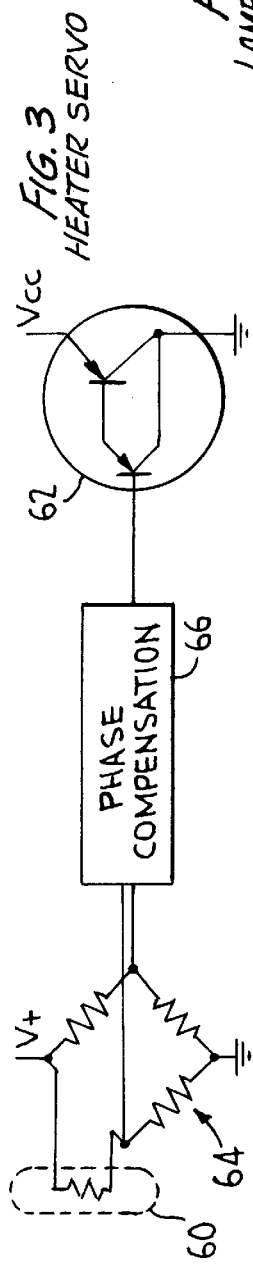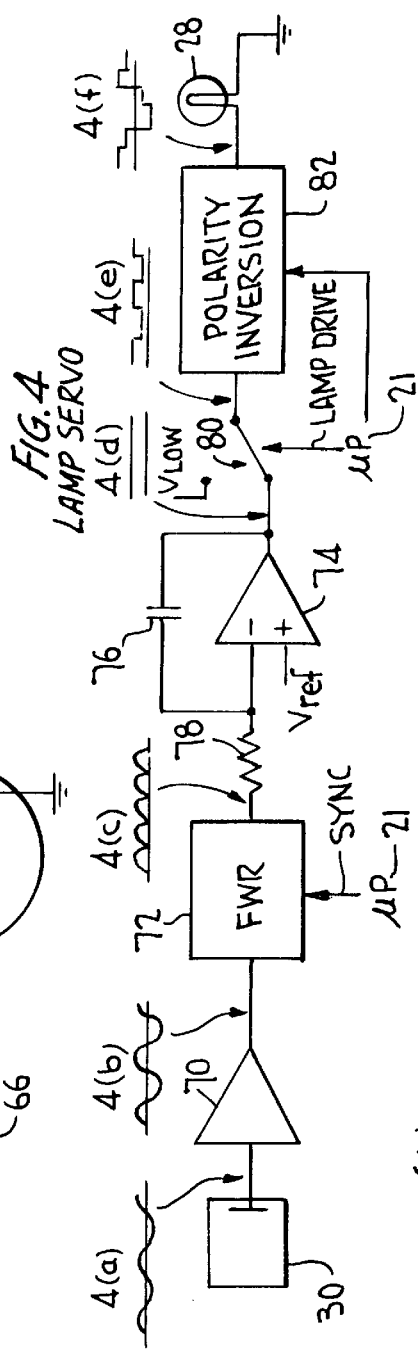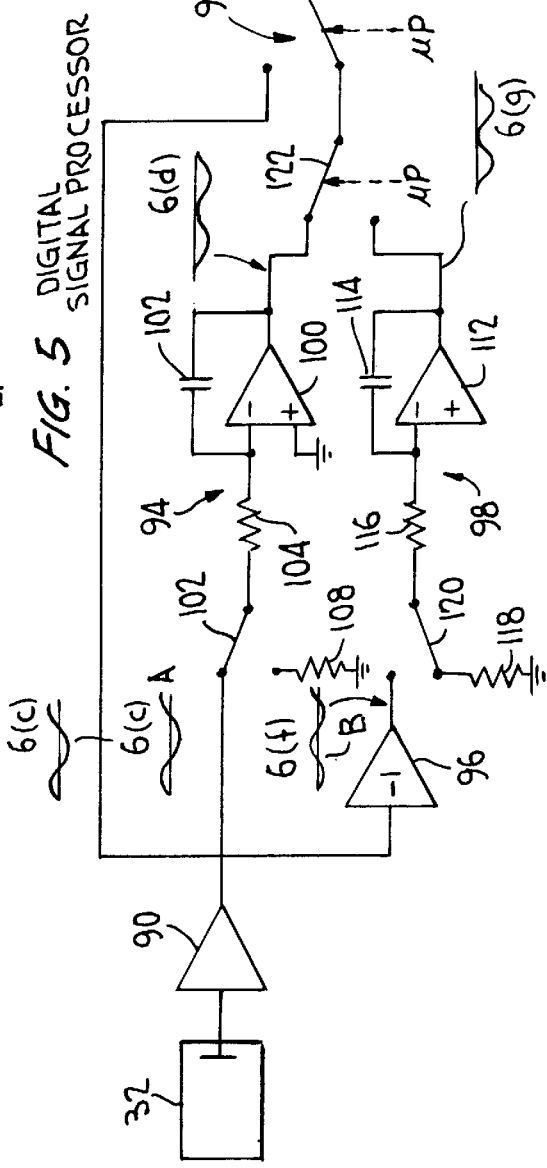

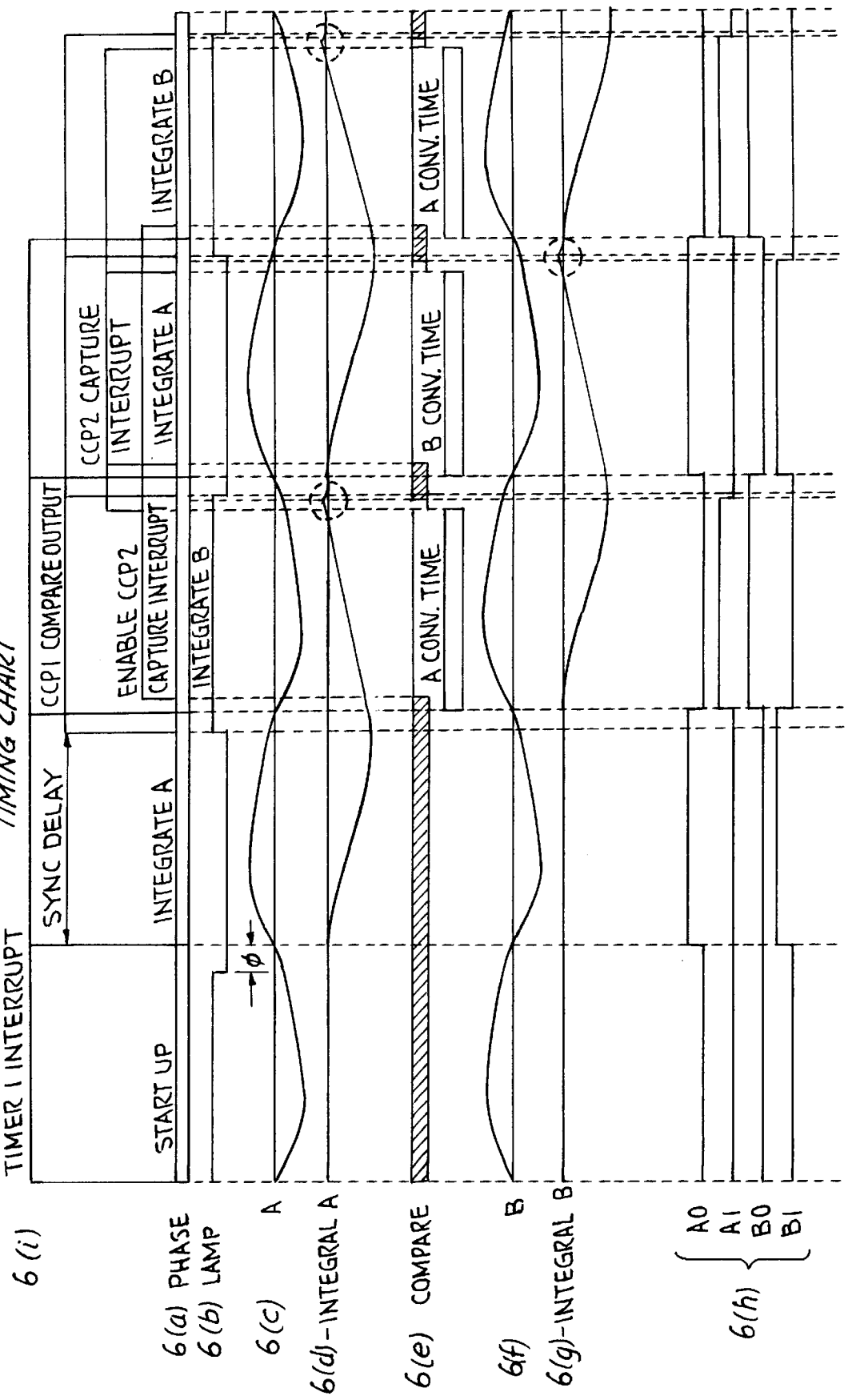

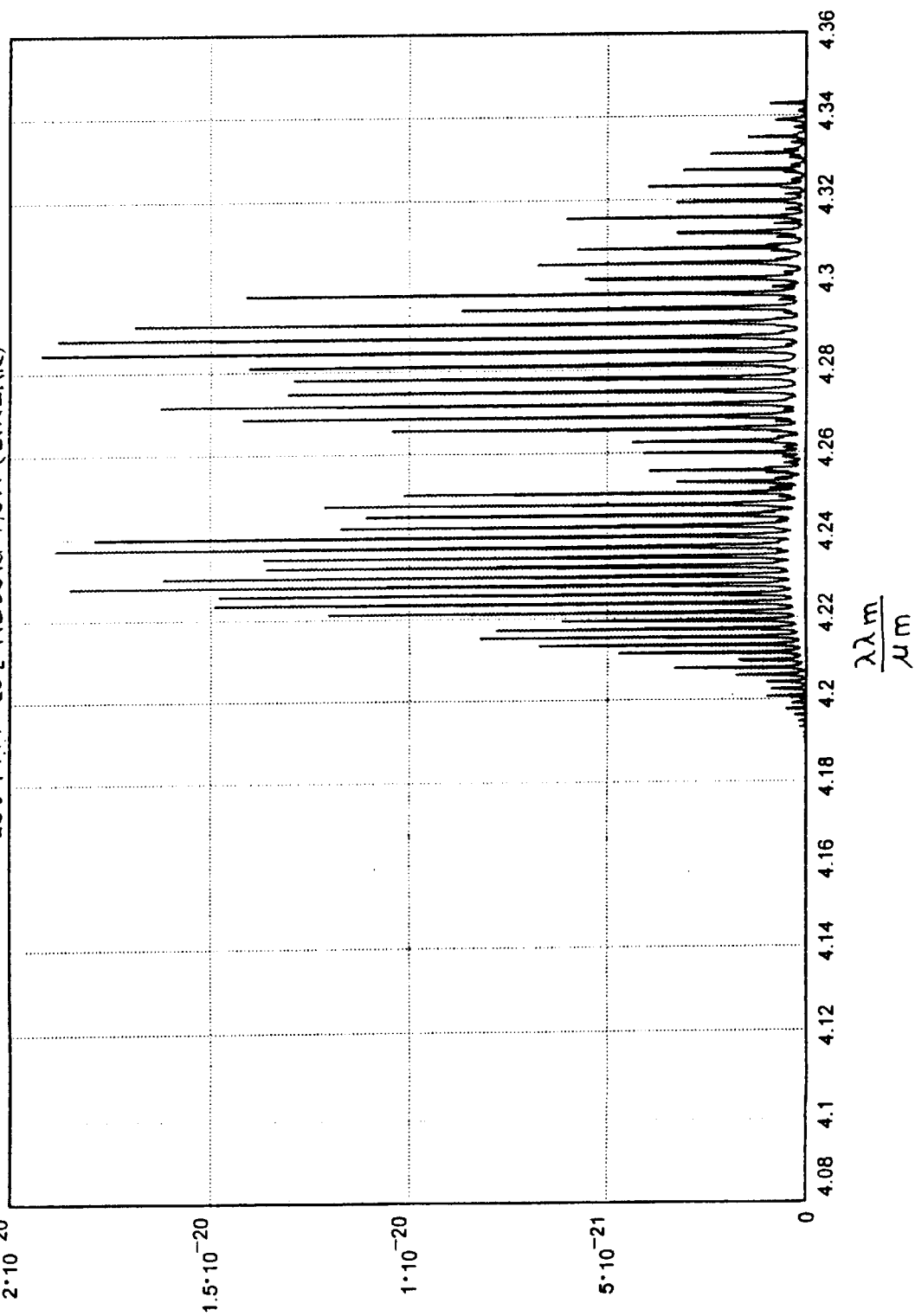

NDIR INSTRUMENT

FIELD OF THE INVENTION

This invention relates to an improved instrument for non-dispersive infrared (NDIR) measurement. More particularly, the invention relates to apparatus and methods for NDIR measurement of the absorption of infrared radiation by gas samples.

BACKGROUND OF THE INVENTION

Non-dispersive infrared radiation (NDIR) measurement techniques have been known for many years as highly useful in analysis of certain gas mixtures. More particularly, infrared radiation is absorbed selectively by certain gas species of interest in a wide variety of circumstances. For example, NDIR measurement of the absorptivity of infrared radiation by carbon dioxide-containing gas mixtures is employed by instruments for measuring the total organic carbon content of water. NDIR measurements of carbon dioxide and other gases, such as carbon monoxide, are also commonly used to monitor atmospheric conditions and to analyze automotive exhaust gases.

More particularly, the total organic carbon content of a sample of water can usefully be measured by adding oxidizers to the water, oxidizing the carbon in the water by exposure to ultraviolet radiation, and separating the carbon dioxide thus formed from the water sample by diffusion across a gas-permeable, water-impermeable membrane into a stream of carrier gas of known composition, commonly carbon dioxide-free nitrogen. This mixed gas sample is then admitted to the cell of an NDIR instrument for measurement of the proportion of carbon dioxide present.

To measure the amount of, for example, carbon dioxide in a mixture with nitrogen employing the basic NDIR principle, an infrared source is provided at one extremity of a closed cell containing the mixture and a suitable detector at an opposite extremity of the cell. Because carbon dioxide absorbs infrared radiation of certain wavelengths, and nitrogen does not, the concentration of carbon dioxide present in the mixed gas sample can be selectively measured by measurement of the transmission through the sample of infrared radiation at wavelengths absorbed by carbon dioxide.

Typical NDIR instruments measure carbon dioxide absorption in a narrow bandwidth around 4.3 microns. Wavelength selectivity is commonly achieved through the use of multiple-layer interference filters between the sample and the detector. If an on-line calibration process is carried out periodically, e.g., using pure nitrogen to "zero" the instrument, or if another method is provided to ensure that the intensity of the source remains constant over time (variations in the infrared source being the most significant cause of long-term drift) accurate relative measurements of the carbon dioxide content of the mixed gas stream can be made.

Infrared detectors responsive to 4.3 micron, i.e., 4300 nm, radiation include quantum photovoltaic and photoconductive detectors, gas-filled detectors such as bolometers and Golay cells, and thermally-responsive thermopiles and pyroelectric detectors. Of these, pyroelectric detectors are the most compact and least expensive, and are therefore commonly used in low-cost NDIRs.

Pyroelectric detectors comprise a piezoelectric crystal arranged to be heated by the incident radiation to be measured. The crystal provides a voltage signal responsive to the rate of change of the temperature of the crystal, e. g., due to heating by the incident radiation; the signal is independent of the wavelength of the incident radiation. As the output signal is responsive to the rate of change of the temperature of the crystal of the pyroelectric detector, a modulated light source is required to produce an output responsive to absorption of radiation by a gas sample. Modulation is typically accomplished either by employing a mechanical chopper, e.g. a spinning disk with slots disposed in the path of the light between the source and detector, or by electrically modulating the light source on and off.

The usual source of 4.3 micron light in NDIR instruments is an electrically heated element that serves as a black-body radiator. Silicon carbide rods have been used as low color temperature filaments, that is, to provide a 350–400 degree Kelvin, i.e., K. source whose maximum intensity is about 4.3 microns. Nichrome and Kanthal filaments have also been used, either in air or an inert atmosphere, as low color temperature infrared sources. These elements typically have relatively high thermal capacities and therefore require the use of an optical chopper to modulate the light.

Recent low-cost NDIR instruments have employed the low thermal capacity filaments of standard miniature incandescent lamps as high color temperature sources that can be electrically modulated, thereby eliminating the need for bulky and mechanically unreliable optical choppers. Although most of the radiation emitted by these lamps is in the visible portion of the spectrum, far outside the infrared range of interest in NDIR instruments, the low thermal mass of their filaments and the fact that they operate in a vacuum nonetheless leads to greater efficiency than low color temperature alternatives. Additional measures, however, are generally required to effectively block the visible portion of the spectrum.

Interference filters for $CO_2$ detection, that is, as used to ensure that only radiation absorbed by $CO_2$ is incident on the detector, are also readily available, either integrated directly into a pyroelectric detector package or as a separate window. The -113 filter from Eltec Instruments, Inc., Daytona Beach, Fla., for example, is an optional filter for their pyroelectric detectors that is specifically offered for $CO_2$ monitoring; this filter has a transmission bandwidth from 4.183 to 4.353 microns. However, as discussed in detail below, this filter is not optimal for this purpose.

NDIR instruments now available fall generally into several classes. A first class of relatively expensive NDIR instruments typically employs an infrared-emitting filament as the source, a mechanical chopper to modulate the beam, and one or two infrared detectors, with suitable filters.

Instruments comprising two detectors typically include two separate cells defining beam paths of equal length. One cell is filled with a non-infrared-absorptive gas, providing a "reference path", and the other with the sample; the signals provided by the detectors are then compared in a ratiometric determination of the absorption. Such instruments can be made to work well, but are complex, bulky, and expensive. Furthermore, accurate measurements can be made only if the temperatures of both detectors are maintained equal, and if the detectors age in substantially identical fashion over time; neither condition can be ensured conveniently. Moreover, as the signals provided by pyroelectric detectors are relatively noisy, such two-detector instruments inherently possess substantially more noise than single-cell instruments.

Comparatively less expensive single-cell NDIR instruments now available commonly employ an electrically-modulated incandescent lamp mounted at one end of a tube as the infrared source, and a pyroelectric detector comprising an interference filter at the opposite end to measure the amount of infrared radiation passing through a sample in the tube. The inner surface of the tube is commonly gold-plated to ensure consistent high reflection of the infrared radiation as it travels along the tube from the source toward the detector.

A first type of single-cell instruments, which are relatively inexpensive and therefore popular, do not provide any compensation for instrument drift over time. These instruments typically use an offset gain stage, wherein the signal responsive to infrared intensity is subtracted from a constant and then amplified. In this manner an attenuation of between zero and, for example, 10% of the incident light intensity can be mapped as a zero-to-full-scale output. As described in detail below, the output of this type of system is normally a difference voltage. The principal disadvantage of this method is that because the output difference voltage is proportional to the incident light intensity, as the lamp ages and its output changes, the readings will change in proportion producing substantial gain errors. A second disadvantage is that the output is proportional to the system gain, causing the output to drift with component aging or temperature-induced changes in the gain stages. A third disadvantage is that lamp aging and the corresponding reduction in light output substantially reduce the dynamic range of the instrument.

A more sophisticated form of single-cell instruments, on the other hand, typically provide movable filters or other means for controlling the wavelength of the radiation incident on the sample between a first "reference" wavelength not absorbed by the sample and a second "measurement" wavelength that is absorbed by the sample; a ratiometric calculation is then made to determine the proportion of absorptive gas in the sample. Such instruments involve moving parts and are subject to various mechanical difficulties, leakage, and the like. Further, although the noise in such systems is low relative to that exhibited by the dual-detector instruments discussed above, and use of a single detector eliminates problems inherent in use of two detectors that may or may not be precisely matched, no provision is usually made to ensure the long-term stability of the source.

Further improvements in NDIR instruments of this type are shown in FIG. 5 of Small et al, "Oxidation and detection techniques in TOC analysis", *Am. Lab.* 18(2), February 1986, pp. 141–150; Small suggests that automatic gain control can be used to control the lamp intensity, presumably to improve the long-term accuracy.

Other known NDIR instruments combine elements of both types discussed above. For example, Passaro et al U.S. Pat. No. 4,687,934 shows an NDIR instrument adapted for measurement of several components of automobile exhaust streams. (Earlier Passaro U.S. Pat. Nos. 4,346,296 and 4,398,091 are generally similar.) The Passaro instrument employs a mechanical chopper to modulate the infrared radiation from the source, while several detectors are provided at the opposite end of a sample tube. Each detector is provided with a different interference filter, rendering the detectors selective for the exhaust components of interest. Calibration is provided by introduction of either a "zero" gas, i.e., one known to be infrared-transparent, or a sample gas of known composition, and adjusting the instrument output accordingly, and is accomplished either at predetermined intervals or when a thermistor indicates a drift in ambient temperature of more than 6° C. The degree of inaccuracy inherent in this approach would be unacceptable in many applications.

The measurements of concentration of carbon dioxide (and other gases) in gas samples provided by all prior art NDIR instruments known to the inventor also suffer from certain inherent inaccuracies in the signal processing techniques employed, as follows.

A first source of inaccuracy inherent in the design of all known prior art NDIR instruments occurs when these instruments employ a well-established equation known as Lambert's Law to calculate the $CO_2$ concentration, as follows:

$$I = I_0 e^{-abc}$$

where:
 I=measured light intensity at the detector
 $I_o$=light intensity at the source
 a=absorption coefficient
 b=path length
 c=$CO_2$ concentration In fact, the present inventor has determined that the direct application of Lambert's Law, as usually applied to measurements of carbon dioxide by measuring the absorption of infrared radiation from a non-monochromatic source, is not accurate. (The same is true of the usual use of Lambert's Law to measure the concentration of other gases.) The inaccuracy arises because the absorption by $CO_2$ of infrared radiation in a band of wavelengths centered around 4.3 microns is incomplete. Rather than absorb a wide bandwidth of wavelengths centered on 4.3 microns, the absorption spectrum of $CO_2$ is comb-like, as shown in FIG. 7 of this application. Therefore, a substantial fraction of the wide-bandwidth infrared radiation provided by the usual incandescent filaments or other black-body radiators "leaks" past the $CO_2$ and heats the detector. As the usual calculations performed to determine the $CO_2$ effectively assume that the absorbtion is a simple function of the $CO_2$ concentration, the measurements are inaccurate.

Research by the present inventor has shown that this light "leakage", i.e., the proportion of the infrared radiation that is within the passband of commercially available interference filters designed specifically for $CO_2$ absorption measurements, but is not absorbed by $CO_2$, ranges from over 90% (worst case) to about 70% (best case) of the incident light. Hence, regardless of the $CO_2$ concentration, the detector will register significant radiation in the band assumed to be absorbed by $CO_2$. Unless the signal is compensated in some way, the detector's output will underreport the $CO_2$ actually present in the sample; that is, the "leakage" will be misinterpreted as a less-than-correct value for the $CO_2$ content. Most manufacturers make empirical corrections to linearize the readings provided by their instrument, i.e., correct the measurements procided by their instruments to correspond to to calibration measurements performed using samples of known $CO_2$ content. However, to properly and accurately address this problem, a physical theory is needed that addresses the noted deviation.

Second, the interference filters used in commercially available NDIR instruments for measurement of $CO_2$ generally do not take into account the effective frequency shift in the filter passband caused by the wide angle of incidence of radiation on the interference filter. A significant fraction of the infrared radiation transiting a gold-plated sample tube reflects repeatedly from the inner wall of the tube and therefore exhibits a wide angle of incidence on a filter at the end of the tube. This phenomenon has the effect of shifting the pass band of the filter away from the absorption band of $CO_2$, thereby reducing the signal-to-noise ratio.

A further noise-related problem inherent in the design of presently-available NDIR instruments results from inappropriate selection of the lamp drive frequency as effectively required by limitations on the signal processing circuitry typically employed. More specifically, the frequency response of the typical pyroelectric detector has a flat peak extending from around 0.05 hz to about 1 hz, above which it drops off at 6 db/octave, while the emission efficiency of miniature lamps typically employed as infrared sources peaks at about 1 hz. Accordingly, it would be preferred to operate the instrument at a lamp modulation rate of 1 hz or less to achieve the best signal-to-noise ratio.

In a typical prior art design, the AC signal received from the pyroelectric detector is full-wave rectified and then averaged to produce a continuous output. In a circuit of this kind, the averaging time constant must be 5–10 times the modulation period in order to reduce the ripple in the rectified AC signal to acceptable levels. For this reason, prior art designs typically use a lamp modulation frequency of 8 to 10 hz in order to produce an output with a time constant of about 1 second. If these designs were operated at 1 hz (as desired to maximize the lamp emission efficiency, as noted above), the instrument would require an unacceptably long time constant of around 10 seconds. Consequently, such instruments effectively strike a compromise between signal-to-noise ratio and instrument response time.

As mentioned, the pyroelectric sensor typically employed comprises a piezoelectric crystal providing an output voltage responsive to the rate of change of its temperature. Any environmental temperature change communicated to the sensor affects the accuracy of its response to the modulated infrared source. Environmental temperature fluctuations that reach the miniature lamps typically employed also cause changes in the radiation levels emitted. Various prior art designs typically put the lamp directly into the gas stream in the sample tube, and some even put the pyroelectric sensor in the gas stream. To minimize the effect of environmental temperature fluctuations, it would be preferable to thermally isolate both the lamp and the detector from the gas stream, and to provide precise temperature control of both.

Most prior art NDIR instruments, particularly low-cost designs, use a switched unipolar supply for the lamp. This results in accelerated filament degradation known as "DC notching", caused by surface migration of tungsten, and generally severe distortion of the filament shape over time. Both the spectral output and the distribution of the light can be substantially affected, leading to variations in the amount of 4.3 micron radiation reaching the detector. As is well known in the lamp art, operating the lamp on a bipolar supply nearly eliminates the effects of tungsten migration and preserves the original shape of the filament for a much longer time.

It will be appreciated from the foregoing that present-day NDIR instruments can be improved in numerous respects.

OBJECTS OF THE INVENTION

It is therefore an object of the invention to overcome the various deficiencies of the prior art; more particularly, it is an object of the invention to provide an NDIR instrument having increased accuracy and greater reliability and longevity than the less expensive prior art NDIR instruments discussed above, and that is smaller, simpler, and of less costly construction than the more expensive prior art instruments, while exhibiting no loss of accuracy.

It is a more specific object of the present invention to accurately describe the deviation from Lambert's Law exhibited by the absorption of 4.3 micron infrared radiation by $CO_2$ (and similar deviations exhibited by other gases), and to employ this knowledge both to measure the efficacy of various interference filters with respect to light leakage, allowing optimal selection of the interference filter to be employed, and to properly calibrate an NDIR instrument, such that no empirical linearity correction is needed.

It is a further object of the invention to determine the correct interference filter for use where multiple reflections of the light along a tube containing the sample cause effective displacement of the passband of the interference filter.

It is a further object of the present invention to provide a signal processing circuit allowing the use of a modulation frequency of 1 hz or less while achieving an instrument response time of less than one second, thereby increasing the system signal to noise ratio, by utilizing the maximum output of both the lamp and pyroelectric detector.

A further object of the invention is to provide a simple, compact NDIR cell and associated heater circuits that precisely correct for any environmentally induced temperature fluctuations of either the lamp or the pyroelectric detector, to reduce noise and improve reading-to-reading repeatability.

Yet a further object of the invention is to provide a bipolar supply for driving the lamp, to minimize lamp aging, and to integrate this bipolar supply into a low-cost dual beam NDIR instrument design for long term baseline drift compensation.

It is a further object of the invention to provide an optimized single-cell NDIR, preferred for use where a supply of non-absorptive gas is available for regularly "zeroing" the instrument, as well as an optimized dual-beam instrument, for use where such a gas supply is not available, and providing other means for ensuring long-term stability.

Other objects of the invention will appear as the discussion below proceeds.

SUMMARY OF THE INVENTION

1. Derivation of Correct Absorption Equations

The absorption of infrared radiation of wavelengths around 4.3 microns by $CO_2$ is shown in FIG. 7. FIG. 7 represents a graphical version of tabular data presented in NASA Reference Publication 108.4, *Atlas of Absorption Lines from 0–17,900 $cm^{-1}$*. As can be seen by the inverted comb-like peaks, $CO_2$ does not absorb radiation continuously over any range of wavelengths that includes more than one peak. As most $CO_2$ interference filters have a passband of 100 nm or more, encompassing most or all of the absorption spectrum shown, only a portion of the light passing through the filter is actually absorbed by $CO_2$, regardless of the $CO_2$ concentration. The fraction of the total light that is not absorbed by $CO_2$ is referred to as the "Leakage" light L.

As discussed above, Lambert's law of absorption $$I=I_0 e^{-abc}$$

where:
 I=measured incident light intensity
 $I_0$=measured incident light intensity, with c=0
 a=absorption coefficient of $CO_2$
 b=optical path length
 c=concentration of $CO_2$ assumes either monochromatic light or continuous absorption of the light across the passband by the absorbing species. Neither circumstance is correct with respect to present-day NDIR instruments. Rewritten to include light leakage L, the above equation appears correctly as:

$$I=I_0 L+I_0(1-L)e^{-abc}$$

where L=Light Leakage factor

The first term is the fraction of the incident light that is not absorbed by $CO_2$ (regardless of concentration) and the second term is the fraction that is actually absorbed.

As referred to briefly above, the lowest-cost currently available NDIR instruments typically use an offset gain stage, wherein the signal responsive to IR intensity is subtracted from a constant and then amplified. In this manner an attenuation of between zero, and, for example, 10% of the incident light intensity can be mapped as a zero-to-full-scale output. The output of this type of system is a difference voltage:

$$V - V_0 = (1 - e^{-abc})I_0 K(1-L)$$

where:
V=output voltage
$V_0$=output voltage with c=0
K=system gain

The principal disadvantage of this method is that the output difference voltage is proportional to the incident light intensity, $I_0$. Accordingly, as the lamp naturally ages and its output changes, the readings will change in proportion, producing substantial gain errors. A second disadvantage is that the output is proportional to the system gain K, causing the output to drift with component aging or temperature-induced changes in the gain stages.

A third disadvantage is that lamp aging and the corresponding reduction in light output will substantially reduce the dynamic range of the instrument. For example, assume the offset gain is set such that 10% attenuation equals full-scale instrument output, as is typical. If the lamp output diminishes by 5%, the measured intensity will be reduced to approximately ½ the full scale value with no $CO_2$ present, leaving only half the dynamic range available; if the lamp intensity diminishes by only 10%, the instrument will cease to function altogether.

It is, however, interesting to note that by using this offset-gain method, the light leakage factor L becomes a simple gain multiplier and is effectively included in the empirical gain factor K. It appears likely that this offset-gain method has found almost universal acceptance in current low cost NDIRs, despite its very significant drawbacks as noted above, because the discrepancy in Lambert's law due to light leakage, as detailed above, can be resolved by a simple gain adjustment. Indeed, resolution of the discrepancy in Lambert's law is thus achieved without explicit realization that the discrepancy exists, much less understanding it in detail.

In contrast, and as detailed below, the output of the signal processing circuit of the present invention is a 16-bit digital value directly proportional to detected infrared intensity with no offset, i.e. the detection circuit provides a full scale output when $I = I_0$. According to this important aspect of the invention, a 10% change in detected intensity can be measured with over 12 bit resolution over the entire measurement span of the instrument. Thus, even if the lamp intensity is reduced by 50%, the instrument will continue to function with full dynamic range and accuracy.

The output, in this case, is a ratio of numbers:

$$\frac{N}{N_0} = L + (1-L)e^{-abc}$$

where:
N=output reading
$N_0$=output reading with c=0

Note that the output ratio is not dependent on either system gain or lamp intensity. It depends solely on the light leakage factor L which is a function of the inherent absorption characteristics of $CO_2$ and therefore constant. A mathematical method for determining this light leakage factor L during calibration is given below. The accurate knowledge of L determined during development of this invention also provides a quantitative method for evaluating the effectiveness of various interference filter designs, e.g., lower values for L imply a better match of the filter to the $CO_2$ absorption spectrum.

2. Selection of Interference Filter

It will be apparent that a considerable fraction of the light emitted by a lamp at one end of a tube containing a sample gas will reflect several times from the interior wall of the sample tube before being incident on the detector; indeed, the inside walls of sample tubes of NDIR instruments are commonly gold-plated to increase their reflectivity and thus improve the signal-to-noise ratio, and the same is preferred according to the present invention. Assuming a 2 inch long sample tube of ¼ inch inside diameter, and using an Eltec Model 406 pyroelectric detector, the optical energy transfer function displays a sharp peak corresponding to an optical path including 5–6 reflections, resulting in an average angle of incidence of about 30 degrees.

Due to the nature of the interference filters, their passbands are shifted depending on the angle of incidence. The passbands of interference filters are typically specified with zero degree angle of incidence; a passband thus specified is shifted downward about 70 nm given an angle of incidence of 30 degrees. Consequently, the passband of a filter centered to pass both the major "humps" of the $CO_2$ absorption pattern around 4.3 microns (as illustrated in FIG. 7), such as the Eltec-113 filter referred to above, would be shifted substantially below center when placed at the end of a gold tube, and would be less efficient with regard to light leakage. The optimum design according to research by the present inventor is to use a filter whose normal angle of incidence passband is centered around and encompassing the upper major absorption hump, such that its overall passband is shifted to include both upper and lower absorption humps with increasing angle of incidence.

3. Optimal Detector and Lamp Drive Circuitry

The principal components of the circuitry of the instrument according to the invention are a microprocessor to effect all control and signal processing, a programmable constant-current bipolar lamp driver that flashes the lamp at a fixed frequency, e.g., 1 hz, a pyroelectric amplifier followed by dual synchronous rectifiers (one for each polarity), and dual synchronous dual-slope A-D converters.

In operation, the microprocessor produces a precise 1 hz square wave signal named 'Lamp drive' to switch the lamp current source between an 'On' current and a lower 'Idle' current, the Idle current being selected to keep the filament just warm, thus extending the lamp life. In addition, the microprocessor generates a lamp polarity control signal at ½ the lamp frequency that switches the direction of the current through the lamp. This serves to keep the average DC voltage across the lamp at zero volts to prevent surface migration of the tungsten on the filament.

A third timing signal provided by the microprocessor and named 'Sync' switches the dual synchronous rectifiers on the output of the AC pyroelectric input amplifier so as to produce integral half-cycles of the AC pyroelectric signal of each polarity. This Sync signal is the Lamp drive signal delayed in time to precisely accommodate time lags associated with both the lamp and the pyroelectric detector, typically on the order of 400 ms. The microprocessor determines this delay automatically during a 'synchronization' phase of operation of the instrument during which the microprocessor monitors the zero-crossings of the pyroelectric signal in relation to the lamp drive signal.

Each of the two synchronous detectors thus produces an output signal including half-cycles of one polarity (similar to the output produced by a half-wave rectifier), the two outputs being 180 degrees apart. The positive half-cycles are fed to a first dual-slope A/D converter that alternately integrates the positive half-cycle on a capacitor, and then de-integrates the capacitor during the wait for the next positive half-cycle. The time required for the capacitor to linearly de-integrate back to zero is proportional to the integral of the signal during the positive half-cycle. This time is measured using a 16-bit digital timer, thus providing analog-to-digital conversion of the integrated intensity signal. The negative half-cycles are first inverted and then processed identically through a second dual-slope A/D converter. In this manner, the synchronous dual A/D converters each provide a 16-bit integral value every half-cycle. In practice, slow changes that affect the pyroelectric detector's AC signal baseline can be compensated for by taking the output as the average of each two successive half-cycles, i.e., integrals of complete cycles.

In one typical application of an NDIR instrument to the measurement of $CO_2$ concentration, one usually desires to measure the entire amount of $CO_2$ produced in an experiment that may last on the order of several minutes. Essentially, this is done by integrating an absorption peak that may extend over this period. Prior art NDIR instruments generally full-wave rectify the AC pyroelectric signal and then average it to produce a slowly varying DC signal directly responsive to the IR intensity and indirectly to the average $CO_2$ concentration. The filter time constant, typically on the order of several seconds, is chosen to keep the ripple below the ultimate resolution of the instrument. If such a device is applied to integrating the area under a temporal peak with a width of, for example, 1 second, the lag produced by the filtering will adversely affect the accuracy of the integral. The instrument according to the present invention, however, returns the actual integral of the signal during each half-cycle and is not subject to the lags introduced by filtering. By controlling the total time over which the integral is taken to be an integral number of half-cycles, an accurate result is immediately available.

4. Cell Mechanical Design

As used in one instrument for measuring the total organic carbon content (TOC) of water, it is convenient to perform a nitrogen baseline measurement before each $CO_2$ measurement, so that the NDIR instrument according to the invention is constantly being calibrated; consequently long-term drift in the output "zero" or "offset" value is not a concern. In this case, a single-beam instrument is preferred. The key parameters for the overall TOC instrument were maximum gain stability and maximum reading-to-reading repeatability; the use of the nitrogen baseline measurements allows very good long-term stability.

In other applications, wherein the baseline is calibrated less frequently, a dual-beam design correcting for lamp variation to compensate for the natural aging process of miniature incandescent lamps is preferred.

a. Single-beam Cell

The cell design according to the present invention comprises a 2 inch long, 0.25 inch inside diameter sample tube, gold plated on the inside, with a lamp disposed vertically at one end and isolated from the gas stream by a sapphire window. Behind the lamp is a front-surface spherical mirror to direct the back hemisphere radiation forward down the tube. The lamp base is thermally attached to an aluminum or brass lamp-end housing and the chamber sealed, preventing thermal pumping and consequent exchange of gases into and out of the lamp chamber and keeping the absorption within the chamber constant. A power transistor is provided in good thermal contact with the lamp chamber to serve as a heating element, and a thermistor is mounted in a small hole in the lamp-end housing, to ensure intimate thermal contact. The temperature, as sensed by the thermistor, feeds a high-gain, tuned servo circuit to drive the heater and maintain the temperature constant.

At the other end of the sample tube, a pyroelectric detector is isolated from the gas stream behind a silicon window. The silicon window is opaque to visible light and serves to block any visible light that may enter the sample tube through the gas inlet/outlet ports. The detector and window are contained in a detector-end housing, again made from aluminum or brass and sealed from the ambient. A similar heating element, thermistor, and servo circuit serve to independently maintain a constant temperature at this detector end of the instrument. The pyroelectric detector is packaged together with an appropriately selected interference filter serving as a window disposed in front of the detector crystal.

The entire assembly is sheathed in closed-cell foam to insulate it from the thermal environment. Since the lamp is itself a substantial heat source, the use of two independent temperature controllers maintains optimum temperature stability and therefore reduces instrument noise.

b. Dual-beam Cell

As noted above, in applications wherein a nitrogen gas stream is available for regular, automatic calibration, slowly changing drift due to lamp aging can be eliminated, and the performance limitation is noise. Because the minimum noise level is due to thermal noise in the pyroelectric detector, the use of a single pyroelectric detector in a single beam design gives the best performance. However, in applications where calibrations can only be performed infrequently, drift due to lamp aging generally becomes a larger source of inaccuracy than the thermal noise. For this reason, the provision of an additional pyroelectric detector at the lamp end to stabilize the lamp output becomes advantageous.

In the "dual-beam" instrument design according to the present invention, a second pyroelectric detector replaces the mirror in the single-beam design discussed above. A sapphire window and a silicon window are disposed between the lamp and the second pyroelectric detector, so that both detectors "see" the source through optically identical paths. The space containing the lamp, between the tube-facing and rear-facing sapphire windows, is sealed from the ambient, again to prevent the exchange of gases with the ambient. Since the optical path lengths between the lamp and the respective windows are both very short, on the order of 0.05 inches or less and the chamber is pressure sealed, the absorption is low and, more significantly, precisely constant.

The lamp-end pyroelectric detector and the lamp are part of a novel servo circuit that maintains the incident 4.3 micron radiation constant by modulating only the On current of the lamp while keeping the Idle, i.e., keep warm, current constant. Since both pyroelectric sensors view the same filament through identical filtering, sapphire then silicon, the servo circuit ensures that the intensity of 4.3 micron radiation into the sample tube remains constant. In this manner, the dual-beam design offers compensation for lamp aging and long-term stability with only periodic calibrations. Although the noise floor of this design is at least the square root of 2 times that of the single cell design due to the addition of a second pyroelectric detector, in practice noise due to local temperature fluctuations at the lamp end is more significant.

Other aspects and advantages of the invention will be apparent as the discussion below proceeds.

BRIEF DESCRIPTION OF THE DRAWINGS

The invention will be better understood if reference is made to the accompanying drawings, in which:

FIG. 1 shows a cross-sectional view of the NDIR cell of the invention in a single-cell embodiment, and shows its connection to go associated system components;

FIG. 1(a) shows an alternative construction of one end of the cell of FIG. 1, in a dual-beam embodiment;

FIG. 2 shows an end view of the cell of FIG. 1(a);

FIG. 3 shows a block diagram of the servo circuitry provided to maintain the cell at a fixed temperature;

FIG. 4 shows a block diagram of the preferred lamp drive circuit;

FIG. 5 shows a block diagram of the signal processing and analysis circuitry provided to process the signal from the pyroelectric detector juxtaposed to the sample cell;

FIG. 6 shows a timing chart including a number of waveforms, illustrating several signals as functions of time useful in understanding the operation of the instrument of the invention, in particular in the digital embodiment of the signal processing circuitry; and FIG. 7 shows a diagram of the absorption of infrared radiation of wavelengths around 4.3 microns by carbon dioxide.

DESCRIPTION OF THE PREFERRED EMBODIMENTS

Basic Design Considerations

As discussed above, the NDIR cell of the invention may be used in an instrument for measuring the organic carbon content of water, wherein carbon dioxide is generated by oxidation of organic carbon in the water. The $CO_2$ is removed from the water sample in a liquid/gas separator cell, where the $CO_2$ is mixed with a stream of carrier gas of known composition, typically pure nitrogen. The NDIR instrument of the present invention is then employed to measure the absorption of infrared radiation by the mixed gas sample, thus determining the $CO_2$ content of the mixed gas sample and the organic carbon content of the water sample.

NDIR cells are in general very well known. Their fundamental principle is that infrared radiation of particular wavelengths is selectively absorbed by certain gases and not at all by others. In the example described herein, the instrument is optimized for measurement of the concentration of carbon dioxide in a stream of nitrogen, as above; infrared radiation of wavelengths in a band centered on 4.3 microns is selectively absorbed by carbon dioxide, while nitrogen is transparent to infrared radiation in this band. When convenient, as in this circumstance, it is useful to provide pure nitrogen for "zeroing" the NDIR instrument at intervals; a "single-cell" embodiment of the instrument of the invention is then satisfactory.

However, the instrument of the invention can be readily adapted for NDIR measurements of gases other than $CO_2$, and for a number of additional applications. For example, if used to measure $CO_2$, CO (carbon monoxide), unburned hydrocarbons and other constituents of automotive exhaust emissions, it will again usually be convenient to provide a supply of pure nitrogen for periodically zeroing the instrument's response, so a "single-cell" embodiment of the instrument of the invention is again satisfactory. In that use, different interference filters might be provided on a rotating wheel, sliding shutter, or similar arrangement, allowing a single detector to be used to measure the concentrations of different exhaust constituents. See the Passaro patents discussed above.

By comparison, if the teachings of the invention were applied to an NDIR detector optimized for monitoring $CO_2$ concentration in the atmosphere at various locations around the world, such that it would not be convenient to replace a nitrogen supply at, for example, one-month intervals, the instrument might be preferably configured in its dual-beam embodiment, wherein a second detector is provided in a servo loop for controlling the lamp output to be constant over the long term.

As noted above, in typical NDIR instruments, a modulated source emitting 4.3 micron wavelength infrared radiation is arranged at one end of a tube or other chamber filled with a gas sample containing carbon dioxide. An infrared-sensitive detector at the opposite end of the tube provides a signal inversely proportional to the amount of carbon dioxide in the tube. As mentioned above, in the single-beam embodiment of the invention described herein, the tube is first filled with pure nitrogen, which does not absorb infrared radiation. A first measurement is made of the signal from the detector when unattenuated infrared radiation from the lamp reaches the detector. This "zero" value is then compared to a subsequent similar signal recorded when the tube has been filled with a sample consisting of nitrogen mixed with carbon dioxide. The difference value is proportional to the amount of the carbon dioxide present in the gas mixture.

The absorption of infrared radiation by $CO_2$ (and various other gases) is approximately described by an exponential function known as Lambert's Law (also sometimes known as Beer's Law), as follows:

$$I = I_0 e^{-abc}$$

where:
I=intensity of radiation passing through the sample
$I_o$=intensity of radiation incident on the sample
a=absorbtion coefficient (constant for each gas)
b=path length
c=concentration of absorbent gas in the sample A corrected form of Lambert's Law is discussed below under the heading Calibration and Compensation for Light Leakage. The exponential form of the equation remains generally applicable to the discussion following.

The detectors commonly employed for NDIR cells are pyroelectric detectors; the output signal from such detectors is a voltage proportional to the rate of change in the detector temperature. For example, simply directing infrared radiation along a tube filled with a carbon dioxide-containing gas mixture would produce a zero signal from the detector after thermal equilibration. Accordingly, and as discussed above, the usual practice is to provide a square-wave drive signal to the detector by modulating the radiation incident on the gas in the cell, either by a mechanical chopper in the radiation path, or by applying a regular drive signal to the lamp. The temperature of the pyroelectric detector then varies in synchronism with the application of radiation to the gas. The time-varying, approximately sinusoidal AC signal produced by the detector can be rectified and filtered to provide a DC signal inversely proportional to the amount of absorption of carbon dioxide by the gas in the cell. See, for example, the Passaro patents discussed above.

Various presently-available NDIR detectors use frequencies on the order of 3–10 Hz for the lamp drive signal. The lower the frequency employed, the greater the output signal from the pyroelectric detector. This response is exhibited because the detector does not provide an instant response to square wave modulation of the lamp intensity; more specifically, the response of the detector varies in a generally sinusoidal fashion in response to a square wave variation in the intensity of the incident radiation. Furthermore, if the lamp drive signal is electronically modulated between "low" (or zero) and "high" levels, the lamp filament heats up gradually as current is applied, so that both the intensity and wavelength of the emitted radiation vary during the "on" period of the square wave. Accordingly, if a relatively low-frequency drive signal is used, the detector will be heated proportionally more and produce substantially more output. This will accordingly increase the signal-to-noise ratio at the output of the pyroelectric detector, all else being equal. In fact, as mentioned above, the optimum lamp drive frequency with respect to improvement of the signal-to-noise ratio of the detector signal is 1 Hz or less.

As noted above, the output signal of the pyroelectric detector is typically rectified and filtered, or mathematically averaged over time, to produce a DC signal. The lower the lamp drive frequency, the longer the time required for fitering or averaging the signal; accordingly, reducing the lamp drive frequency lengthens the response time of the instrument. It is presumably for this reason that prior art NDIR instruments have normally employed frequencies higher than 1 Hz, consequently suffering decreased signal-to-noise ratios. According to one aspect of the invention, discussed in detail below, a very low frequency, typically 1 Hz, lamp drive signal is used, to maximize the signal-to-noise ratio of the detector signal. This signal is then integrated over each half-cycle of the lamp drive circuit, thus substantially eliminating ripple in the output signal without the necessity of filtering, and providing rapid instrument response.

Further considerations which are relevant to the proper design of an NDIR instrument include the following. Typical incandescent lamps have a positive temperature coefficient, meaning that the filament resistance rises with temperature. Therefore, if one simply applies a square wave drive signal varying between zero and a fixed voltage to an incandescent lamp, the cold filament will draw maximum current when power is initially applied. This high "in-rush" current significantly reduces lamp life. It is known to employ a constant-current power supply to drive the lamp, avoiding the inrush current. It is also known to vary the drive current between "low" and "high" levels, so that the filament never cools completely. Both expedients are preferably adopted in implementation of the invention. However, in the "dual-beam" embodiment of the invention, the "high" level applied is controlled by a servo loop including a second pyroelectric detector, maintaining the intensity of radiation emitted by the lamp constant. This feature, which is believed to be novel, significantly improves the ultimate accuracy of the measurement provided, particularly in circumstances where it is not convenient to repetitively calibrate the instrument by supply of a gas of known concentration.

A further design consideration is the extreme sensitivity of the pyroelectric detector to external temperature. Clearly any amount of cooling or heating due to the environment will adversely affect the accuracy of the measurement. Therefore, an important aspect of the design of the instrument is to ensure that the temperature of the pyroelectric detector varies only in response to incidence of infrared radiation thereon.

Mechanical Design and Temperature Control

FIG. 1 shows a cross-sectional view of the sample cell 22 of a "single-beam" embodiment of the instrument of the invention, wherein a single pyroelectric detector is provided; the instrument is repetitively "zeroed" by comparing the signal provided with a non-absorptive gas in the cell to that provided with a $CO_2$-containing sample. In a "dual-beam" embodiment, a second detector is provided, and used to maintain the lamp output constant over time. The differences between, and comparative advantages of, these two approaches are discussed below. FIG. 1(a) shows an alternate construction of one end of the cell as modified to implement the "dual-beam" embodiment. FIG. 2 shows an end view of the FIG. 1(a) embodiment, illustrating the mounting of the cell 22 between circuit boards 12 and 14 carrying the various components of the lamp drive, heater servo, and signal processing circuitry discussed in detail below.

As mentioned above, the instrument of the invention may be used for NDIR measurement of a variety of gas samples, but is disclosed herein in an embodiment intended for measurement of the carbon dioxide content of gas mixtures. In the preferred single-cell embodiment, the instrument is operated alternatingly to measure the transmission of infrared radiation through the gas mixtures to be analyzed and a non-absorptive "blanking" gas, e.g., nitrogen, to zero the instrument by detecting any drift in the detector used to measure the intensity of radiation passing through the sample gas.

As indicated generally in FIG. 1, the admission and venting of these gases are controlled by valves 18 and 20 under control of a microprocessor ("μP") 21, as are a number of additional functions described further below. It will be appreciated that, depending on the specific implementation of the invention, the microprocessor(s) referred to may be a system-level controller, e.g., as comprised by an associated apparatus providing a series of samples, or may comprise one or more separate microprocessors comprised by the NDIR instrument itself, which may in turn be operated responsive to system commands issued by a system-level controller.

A gas sample to be analyzed (or a pure nitrogen sample, for zeroing the instrument) is admitted to the interior of sample cell 22 by way of an inlet fitting 24 and exits therefrom via an exit fitting 26. Sample cell 22 may comprise a solid block of heat-conductive metal, e.g., brass, having a cylindrical bore therethrough, defining a sample volume. Typical cell dimensions are two inches long, 0.25 inch inside diameter. The inner surface of the bore may be plated with an infrared-reflecting material, such as gold. Valve 20 is normally open during the measurement, and a series of $CO_2$ measurements made over a period of time (up to on the order of one minute) and integrated to obtain the total amount of $CO_2$, e.g., generated in a particular test. However, it is also within the invention to close valve 20 to hold a gas sample static in cell 22, particularly in measurement of mixtures of low carbon dioxide concentrations. This practice eliminates any temperature or density fluctuations occurring if the gas were flowing during the measurement.

A miniature incandescent lamp 28 is mounted vertically in a housing 40 disposed at one end of cell 22, and a pyroelectric detector cell 32 is mounted in a housing 44 disposed at the opposite end of cell 22, as shown. A gold-plated spherical concave mirror 31 is provided to increase the intensity of radiation incident on gas in the sample cell 22. Lamp 28 is sealed within housing 40 by epoxy cement or the like, forming a sealed chamber.

Gas in cell 22 is isolated from lamp 28 by a first window 34 and from detector 32 by a second window 36, sealed between cell 22 and the respective housings by O-rings 46. Window 34 may be of a material transparent to both infrared and visible radiation, such as sapphire; window 36 is of a material transparent to infrared but highly absorbent of visible radiation, such as germanium or silicon. As incident visible radiation also contributes to heating of the pyroelectric detector, and as the wide-spectrum radiation emitted by the low-cost incandescent lamps preferably employed includes on the order of 1000 times as much visible as infrared, such visible-absorbent windows are highly desirable to limit the radiation incident on the detector to infrared only, as well as to filter out any ambient light that may find its way into the cell through the gas inlet and outlet tubes. Provision of the sapphire window at the lamp allows its operation to be verified, e.g., by observation of light leaking into the gas supply tube.

In the "dual-beam" instrument of FIG. 1(a), a second identical detector 30 is provided, disposed in a housing 42. (Housing 42 can be used without modification in the FIG. 1 embodiment.) Detector 30 need not be disposed opposite detector 32 as illustrated, but that shown is the most compact arrangement. Windows 38 and 39 are provided between lamp 28 and detector 30; window 38 is sapphire, which is transparent to both visible and infrared radiation, as is window 34, while window 39 is of the same visible-absorbent, infrared-transparent germanium or silicon material as window 36, to ensure that the paths are optically identical.

The pyroelectric detector(s) 32 and 30 each comprise a sealed "can" 48 containing a pyroelectric element 49 and a further interference filter 50, transparent to infrared radiation in a range centered on 4.3 microns but substantially absorptive of other light. Suitable pyroelectric detectors include the model no. 406 from Eltec Instruments, fitted with the model-43 interference filter, while the lamp 28 may be a Gilway model 4115-2A lamp. Detectors 30 and 32 are centered within recesses in their housings 42 and 44 respectively by further O-rings 52.

The selection of the interference filter is important. Light from the lamp travels down along the cell, reflecting from the interior wall surface. Depending on the number of reflections, the light may arrive at the detector at a substantial angle of incidence. This has the effect of moving the passband of the interference filter downwardly, by about 70 nm at an angle of incidence of 30°. Accordingly, the interference filter should be selected to have a nominal passband wide enough to accept this "shifted" radiation; the model-43 from Eltec Instruments, mentioned above, is satisfactory for measurement of absorption of infrared radiation in the range around 4.3 microns by $CO_2$ by the instrument described above.

As mentioned above, it is important to accurate measurements that the entire instrument, and the gas sample and detector(s) in particular, be maintained at a constant temperature. To this end, the entire instrument is encased in closed-cell foam 70 (FIG. 2) to isolate it from the ambient atmosphere. Cell 22, and housings 40, 42, and 44, are all fabricated of highly heat-conductive materials. Cell 22 may be brass, and the housings 40, 42, and 44 of aluminum. These elements are fabricated and assembled so that they are in good heat-conductive relation with one another. Similarly, detectors 30 and 32 are urged by the corresponding O-rings 46 against spacers 54 of a heat-conductive, electrically insulative material, interposed between detectors 30 and 32 and their respective housings 42 and 44, to ensure temperature stability of the detectors. The three conductors 56 of each detector pass through apertures in the spacers and the respective housings; the detectors may be further secured to their housings by thermally-conductive, electrically-insulating epoxy disposed around conductors 56.

Temperature control of the entire assembly is provided by two identical heater servo circuits, one of which is illustrated schematically in FIG. 3. Each servo circuit includes a thermistor 60, providing a resistance varying with temperature, and a power transistor 62 driven by the servo circuit to maintain the thermistor at a preset temperature. As can be seen in FIG. 2, illustrating the "short side" end of the FIG. 1(a) assembly (the "long side" being essentially identical, in both single- and dual-beam embodiments) the thermistors 60 are mounted in wells in housings 42, while the power transistors 62 are secured directly to housings 42. The thermistors 60 may be the model 10K3MCD1 from Betatherm, of Shrewsbury, Mass.; this thermistor is very small and has a correspondingly fast response time, allowing high gain to be employed in the heater servo loop. The current through power transistors 62 is controlled by the circuit of FIG. 3 so that the temperature of thermistors 60, also in good thermal contact with mounting blocks 42, 44 is constant, thus completing the servo loops. Transistors 62 are provided in the industry standard "TO-220" package, designed for efficient heat transfer to a flat mounting surface. Accordingly, heat dissipated by each transistor 62 responsive to current passing therethrough is efficiently transferred to the corresponding mounting blocks 42, 44.

As shown in FIG. 3, each thermistor 60 is connected in a conventional bridge circuit 64, for measuring its resistance; the relative value thereof is passed through a phase compensation network 66, to provide rapid servo response without overshooting the desired setpoint of the temperature, and forms the gate input to transistor 62, completing the servo loop. Accordingly the temperature of the entire assembly is maintained constant within a high degree of accuracy.

FIG. 2 also illustrates the manner in which the cell assembly 10 detailed above is mounted between circuit boards 12 and 14, which carry the components (other than those shown specifically in FIGS. 1 and 2) implementing the circuits described by the block diagrams of FIGS. 3–5. In general, "cell" board 12 carries the lamp drive, heater servo, and detector signal rectification and filter circuitry; FIG. 2 illustrates the manner in which the pyroelectric detectors 30 and 32, thermistors 60, and transistors 62 are connected directly to the corresponding circuits on board 12. Lamp 28 is connected similarly. "Controller" board 14 carries microprocessor 21 and related circuitry to control the sequence of operations, provide communication with associated instruments, and the like. As shown, the cell assembly is spaced from boards 12 and 14 by standoffs 68 at the center of cell 22; cooperating connectors on both boards mate to carry various signals therebetween. The entire assembly is encased within a box formed of bonded sheets of insulative material, such as closed cell urethane foam board, as indicated at 70.

Lamp Drive Circuit

FIG. 4 shows the preferred embodiment of the servo loop circuit used to drive the incandescent lamp 28 in the dual-beam embodiment of the instrument of the invention, so that the lamp output remains constant over time. (As discussed above, in the single-beam embodiment, variation in the lamp output is corrected by measuring the intensity of radiation incident on the detector with a non-absorbent gas in the cell.) Waveforms 4(a)–(f) shown in FIG. 4 correspond to the amplitude of signals present in the associated conductors as functions of time.

Thus, signal 4(a) provided by "short side" pyroelectric detector 30 in response to the square-wave modulated infrared radiation emitted by lamp 28 is first amplified in amplifier 70. The amplified signal 4(b) is then rectified by a full-wave rectifier 72, operating to invert alternate half-cycles of the incoming signal responsive to a synchronization signal "SYNC" provided by microprocessor 21. The rectified signal 4(c) is then compared to a setpoint provided by a fixed voltage $V_{ref}$ by an integrating difference amplifier comprising op-amp 74, capacitor 76, and input resistor 78, connected as shown. The output is a DC signal 4(d) of level corresponding to the intensity of radiation falling on the "short side" detector 30 during the "high" periods of the lamp drive signal, servo-controlled to equal $V_{ref}$.

A switch 80 controlled in response to a LAMP DRIVE signal provided by microprocessor 21 switches the lamp drive signal between the "high" level set by signal 4(d) and a low level $V_{low}$, thus keeping the lamp filament warm during periods of low radiation emission, lengthening its life as compared to switching between "on" and "off" states. The resultant signal 4(e) alternates between the "high" level set by reference to $V_{ref}$ and the low level $V_{low}$.

Providing an AC signal to the lamp 28, as opposed to the DC signals commonly used in the prior art, substantially lengthens the life of lamp 28, apparently by preventing migration of the tungsten of the filament. If a unipolar DC supply is used, the tungsten appears to migrate along grain boundaries, forming notches that weaken the filament. Therefore, alternate cycles of the square wave lamp drive signal are inverted in a polarity inversion unit 82, providing an AC square wave lamp drive signal 4(f). The polarity inversion unit 82 may comprise a conventional "H-drive" circuit arrangement.

In the single-beam embodiment, the lamp drive circuit again provides a bipolar drive signal varying between low and high levels. In this case, a constant-current supply is used, to avoid high inrush currents occurring on switching between the low and high levels, which reduce lamp life. As noted above, in this embodiment, variation in the lamp output is corrected for by measuring the intensity of radiation incident on the detector with a non-absorbent gas in the cell; no adjustment in the lamp output per se is needed.

As mentioned, in the preferred embodiment, the frequency of the LAMP DRIVE signal is 1 Hz, giving the lamp 28 a relatively long period of time to heat, and the pyroelectric detectors 30 and 32 time to sense change in their temperatures proportional to the amount of infrared lamp radiation incident thereon, increasing the signal-to-noise ratio of the output signals from the detectors.

Where not indicated to the contrary, it is also within the scope of the invention to mechanically modulate the intensity of radiation incident on the cell and pyroelectric detector(s), using a motor-driven chopper or the like.

Processing of Pyroelectric Detector Signal

FIG. 5 shows the digitally-controlled circuit used in a preferred embodiment of the invention to derive a DC voltage proportional to the amount of radiation incident on the detector 32, and hence inversely proportional to the absorption of radiation by carbon dioxide (when a sample is present) in the NDIR cell. As in FIG. 4, the waveforms shown in FIG. 5 correspond to the amplitude of signals present in the associated conductors as functions of time; FIG. 6 shows more detailed views of a number of the signals shown in FIG. 5, and also illustrates their respective relations in time.

Referring now to FIG. 5, the AC input signal from detector 32 is amplified by amplifier 90. The amplified signal, referred to in this connection as signal A, and shown in detail by FIG. 6(c), is passed to a first dual-slope inverting integrator 94. Signal A is also inverted by inverter 96; the inverted signal B, shown in FIG. 6(f), is supplied to a second dual-slope inverting integrator 98. Signal A is also connected directly to a switch 92. When switch 92 is in the position shown, one of the integrated signals (6(d) and (g)) is supplied to zero-crossing detector 106; in its alternate position, switch 92 allows the input signal A to be connected to zero-crossing detector 106, for reasons discussed further below.

First dual-slope inverting integrator 94 comprises an op-amp 100, an integrating feedback capacitor 102, and an input resistor 104, as is generally known in the art. Switch 102 remains in the position shown in FIG. 5 during the positive half-cycle of the input signal A, so that during this period charge corresponding to the amplitude of the input signal A is stored on capacitor 102, integrating signal A. FIG. 6(d) shows the integrated inverted input signal, illustrating the variation in its amplitude over several cycles of operation. The period during which the input signal is integrated is denominated Integrate A in FIG. 6(a).

As shown by FIG. 6(c), the input signal A is generally of quasi-sinusoidal form, corresponding to the rate of change in temperature of the pyroelectric detector. The detector temperature signal itself, if plotted, would be of generally sawtooth form, comprising a series of exponential curves. That is, when the lamp current goes "high", the detector temperature initially rises quickly, then more slowly, and finally approaches a stable value. The reverse happens during the "low" portions of the lamp drive signal, as the detector cools. Accordingly, the input signal A, corresponding to the time derivative of the temperature signal, is quasi-sinusoidal, as illustrated in FIG. 6(c). The positive half of input signal A rises to a maximum value during the period Integrate A and then declines to zero, corresponding to the detector having reached a substantially constant temperature. The integrated value of input signal A, termed— Integral A and shown by FIG. 6(d), correspondingly rises to a final value reached when input signal A crosses zero.

The relation of the zero-crossings of the input signal A is fixed with respect to the transitions in the lamp drive signal, as discussed in detail below. A Timer Interrupt signal (FIG. 6(i)), synchronized to the transitions in the lamp signal, is therefore similarly synchronized to the zero-crossings of input signal A, such that the latter need not be detected per se. Switch 102 is inverted from the position shown in FIG. 5, responsive to the Timer Interrupt signal, as the input signal A goes through its zero point; thereafter, charge is drained from capacitor 102 at a constant rate, controlled by the values of precision resistors 104 and 108. Simultaneously, a 16-bit digital timer 110 commences to measure time, i.e., measures the time required for deintegration. This "deintegration" phase of operation is denoted by the legend "A Conversion Time" in FIG. 6(e).

During the deintegration phase, switches 92 and 122 are connected as shown, so that the output of integrator 94, that is, signal—Integral A, FIG. 6(d), is supplied to zero-crossing detector 106. When all charge has been drained from capacitor 102, that is, when—Integral A passes through zero, the value N of the count stored by timer 110 is stored. As noted, the deintegration proceeds at a constant rate, as indicated by the linear shape of signal—Integral A during the deintegration period. The time thus measured is indicative of the total charge stored during the "Integrate A" phase; N is thus a digital value indicative of the total amount of infrared radiation incident on detector 32 during the "high" portion of the lamp drive signal A.

In order to maximize the signal integrated by dual-slope integrator 94, and thus maximize the ultimate signal-to-noise ratio of the instrument, it is important that the entire positive half-cycle of input signal A be effectively integrated by integrator 94. Accordingly, it is important that the integration commence at the zero-crossings of the input signal A. As indicated above, although the zero-crossings of the input signal A are not detected per se, they bear a fixed relationship to the transitions in the lamp drive signal, which in turn are controlled by the Timer Interrupt signal (FIG. 6(i)).

More specifically, FIG. 6(b) illustrates the lamp drive signal LAMP; comparison of this signal to the output signal A (FIG. 6(c)) from detector 32 reveals a phase lag $\phi$ therebetween due to the response time of the lamp to changes in the level of the drive signal, and to the thermal mass of detector 32. In order to maximize the signal-to-noise ratio, it is important that this phase lag $\phi$ be known accurately, to control the operation of the integrators correctly with respect to the lamp drive signal. As the phase lag $\phi$ may vary somewhat from one instrument to the next due to component variations, the phase lag $\phi$ is measured at start-up (that is, whenever the instrument is first powered), simply by resetting switch 92 so that zero-crossing detector 106 can monitor the zero-crossings of the input signal A with respect to the transitions in the lamp drive signal; the microprocessor 21 (FIG. 1) measures the phase lag $\phi$ therebetween, and subsequently controls the timing of the switching of the connections to the zero-crossing detector and other control actions accordingly.

More particularly, as noted, a timer comprised by the microprocessor provides a Timer Interrupt signal (FIG. 6(i)) every half-cycle, that is, every 500 ms in a system operating at 1 hz. After measurement of the actual phase lag $\phi$ during start-up operation, the input signal's zero-crossings coincide with transitions in Timer Interrupt, as indicated, and the transitions in the lamp drive signal are delayed therefrom by the phase lag $\phi$; the measured phase lag $\phi$ is indicated by the period termed Sync Delay in FIG. 6.

In an alternative method for determining the phase lag $\phi$, the phase lag of the lamp drive signal could be varied incrementally with respect to Timer Interrupt during successive lamp drive cycles of the start-up operation, while measuring values of the input signal integrated at times fixed with respect to Timer Interrupt; the maximal integrated value would correspond to the maximum signal obtained, and thus to the preferred phase lag $\phi$.

As the radiation incident on detector 32 is modulated between "high" and "low" levels by the lamp drive circuit of FIG. 4, the detector output signal is an AC signal. (Note that inversion of the polarity of the lamp drive signal, preferred to extend the lamp life as noted above, is not relevant to the processing of the signal from detector 32.) Moreover, as the detector 32 is maintained at a uniform average temperature by the heater servo circuit of FIG. 3, the integrated values of the signal during both half-cycles are equal. Therefore the negative portion of the output signal A can be similarly processed to yield a second value for the total amount of infrared radiation incident on detector 32 during the "high" portion of the lamp drive signal, doubling the amount of data available.

In the embodiment shown, the detector output signal A is accordingly inverted by inverter 96, forming signal B (FIG. 6(f)). Signal B is similarly integrated and deintegrated by a second dual-slope integrator 98, again comprising op-amp 112, capacitor 114, switch 120, and resistors 116 and 118. As above, the inverse of the integrated input signal, termed—Integrate B, is shown in FIG. 6(g). The position of switch 112 is alternated (defining the A Conversion Time and B Conversion Time periods shown in FIG. 6) so that zero-crossing detector 106 can detect zero-crossings of both signals—Integral A and—Integral B, that is, ensuring that the correct one of the outputs of integrators 94, 98 is compared to zero in detector 106 at the appropriate times. Again, the time required for deintegration, as measured by timer 110, is a digital value indicative of the total amount of infrared radiation incident on detector 32 during the "high" portion of the lamp drive signal.

Thus, it will be appreciated that the circuit shown in FIG. 5, and operated as indicated in FIG. 6, rectifies the detector output signal, integrates both half-cycles separately, and provides digital values indicating the amount of radiation incident on the detector as to each. Each digital value can be used directly in calculation of the amount of carbon dioxide in the sample, as discussed in detail below. Still further improvements can be made by simply averaging the series of values provided; the microprocessor 21 can readily perform the averaging function.

As noted, in the preferred embodiment, zero-crossing detector 106 is used to detect the zero-crossing of the signal—Integral B as its deintegration to zero is completed; in the succeeding half-cycle, the zero-crossing of signal—Integral A is detected. As above, the zero-crossings of the signals A and B, which correspond to the beginnings of the respective deintegration periods, are synchronous to the Timer Interrupt signal, which triggers the commencement of each deintegration, while the zero-crossings of the integrated signals mark the completion of the deintegration. The values of the deintegration resistors 108, 120 are chosen such that the deintegrated signals can be ensured to cross zero before the corresponding input signals, preserving the correct ordering of these events.

It will be appreciated that the proper sequencing of operation of switches 92, 102, 120, and 122 is important to the correct function of the circuit of FIG. 5. Switch 92 is only operated in a start-up phase of operation, during measurement of the actual phase lag $\phi$. Switches 102, 120, and 122 are operated by control signals A0, A1, B0, B1 (FIG. 6(h)) provided by the microprocessor responsive to the Timer Interrupt signal (again synchronous to the zero crossings of the output signal A (FIG. 6(c)) and its inverse B (FIG. 6(f)) and the integrated and deintegrated values thereof (FIGS. 6(d) and (g), respectively), as described above. After the start-up mode of operation, the microprocessor 21 sequences the operation of switches 102, 120, and 122 with respect to Timer Interrupt, and thus with respect to the lamp drive signal and the zero-crossings of the input signal, by provision of signals A0, A1, B0, B1 at the appropriate points. Comparison of the signals shown by FIG. 6 will make the sequence of operation of switches 92, 102, 120, and 122, and the operation of the circuit of FIG. 5, clear to those of skill in the art.

The periods during which the signal from the zero-crossing detector 106 is relevant are indicated by the COMPARE signal (FIG. 6(*e*)), shown hatched during the times the output signal of zero-crossing detector is not monitored; at other times, the zero-crossing detector 106 is connected to monitor zero-crossings of one of the integrated signals Integral A and Integral B, depending on the setting of switch 122. As indicated by comparison of FIGS. 6(*d*) and (*g*) to COMPARE, COMPARE changes state when the integrated signal being examined crosses zero.

In order to ensure reliable detection of the completion of the deintegration process in zero-crossing detector 106, the integrated signals are caused to overshoot past zero slightly, by comparison to a positive voltage rather than zero per se, as indicated by the circled portions of the—Integral A and—Integral B waveforms in FIG. 6. The—Integral A and—Integral B signals are then held at zero by grounding the associated capacitor until the subsequent zero-crossing of the input signal, to ensure the integrated values are accurate.

As noted above, in a "single-beam" embodiment, the instrument is operated alternatingly to measure the amount of radiation transmitted through a gas sample including $CO_2$, and a non-absorptive gas, such as pure nitrogen. Typically, the detector is operated for a period of 30 seconds as to the sample, followed by 30 seconds of measurement with nitrogen in the sample cell; as the lamp cycle frequency is 1 Hz, 60 sample values are thus obtained as to each, more than enough to effectively filter any variation due to local variations in concentration of the sample within tube 22, or the like. The value measured while nitrogen is in the cell is then used as a "baseline" value, to calibrate the measurement made with the sample present.

By comparison, in a "dual-beam" embodiment, the lamp intensity is maintained constant by the lamp servo circuit of FIG. 4; performance of the measurement of the intensity of the signal from detector 32 with a non-absorptive gas in the cell is not, strictly speaking, necessary in order to "zero" the instrument. However, doing so allows correction to be made for any variation in the relative conditions of detectors 30 and 32 due to long term drift, compensation for any solarization of windows 34 and 36, and the like.

Referring again to the single-cell embodiment of the instrument, in the event that the phase lag φ between the zero-crossings of the input signal with respect to the transitions in the Lamp Drive signal is not measured accurately in the start-up phase of operation, the total signal integrated will be less than the maximum available. However, this will be equally true with respect to measurements made both with respect to pure nitrogen and with respect to mixed gas samples. Accordingly, measurements of the intensity of the incident radiation made with the pure nitrogen in the cell can nonetheless be compared to similar measurements made with a sample present, to accurately determine the relative concentration of carbon dioxide present. Stated differently, any error in the determination of φ results only in a diminution of the signal-to-noise ratio of the overall instrument.

Given the above disclosure, implementation of this aspect of the invention is similarly within the ordinary skill of the art. Numerous differing implementations of the principles implemented in the circuit of FIG. 5 (and other aspects of the implementation discussed) are within the skill of the art, and are within the scope of the invention except where specifically excluded by the appended claims.

Microprocessor 21 (FIG. 1) may provide a further synchronization signal, e.g., to an associated instrument, providing mixed gas samples for NDIR analysis. As indicated, microprocessor 21 may also control valves 18 and 20 (FIG. 1), controlling the alternate filling of the interior volume of the cell 22 with non-absorptive carrier gas or the mixed gas sample for analysis. Microprocessor 21 may also receive the processed output signal from the circuit of FIG. 5, as indicated, e.g., for calculating the gas concentration in the cell responsive to the level of the filtered signal, as discussed in further detail below, comparing the "zero" value measured while the cell is filled with carrier gas to that measured while it is filled with a mixed sample gas, to detect drift in the response of either detector over time, and for further processing as desired.

Calibration and Determination of Concentration

As noted above, it is the ultimate object of the invention to provide a measurement of the concentration of an infrared-absorbent gas in the sample cell 22. The usual practice in NDIR measurement is to determine the concentration by solution of the equation known as Lambert's Law:

$$I = I_o e^{-abc}$$

where:
I=intensity of radiation passing through the sample
$I_o$=intensity of radiation incident on the sample
a=absorbtion coefficient (constant for each gas)
b=path length
c=concentration of absorbent gas in the sample In implementation of this equation according to the present invention, $I_o$ is the intensity of the "high" portions of the lamp drive signal, (as measured by detector 32 in the single-beam embodiment, with pure nitrogen in the cell, and by detector 30 in the dual-beam embodiment), a is known with respect to various absorbent gases, and b is a simple design parameter of the particular instrument. I is measured accurately by the dual-slope integrator with a sample in the cell, allowing c to be determined.

However, Lambert's Law as set forth above applies exactly only Ad in the circumstance where the gas being measured absorbs all frequencies of the radiation incident on the detector. In fact, the radiation emitted by an incandescent lamp is of broad bandwidth, including a continuous range of wavelengths, while, as shown by FIG. 7, carbon dioxide absorbs only narrow bands of wavelengths. The pyroelectric detector(s) are similarly broad-band. Thus, although the silicon window absorbs the radiation in the visible range, and the interference filter further ensures that the detector "sees" only radiation in a narrow passband centered on 4.3 microns, substantial radiation still leaks through the $CO_2$, regardless of its concentration.

More specifically, FIG. 7 shows the actual absorption spectrum of carbon dioxide between 4.08 and 4.36 microns. As can be seen, rather than absorbing a continuous spectrum of infrared in the range centered on 4.3 microns, as generally assumed by all prior art NDIR instruments of which the inventor is aware, the $CO_2$ absorbtion spectrum describes a series of inverted comb-like peaks; a substantial fraction L of the infrared radiation therefore leaks through the $CO_2$, regardless of its concentration, and is incident on the detector.

The present inventor has realized that even the best filter is incapable of ensuring that the only infrared radiation incident on the detector is of a wavelength absorbed by carbon dioxide; given the "comb-like" absorption spectrum of $CO_2$, it would be impossible to provide a filter absorbing all the wavelengths passed by the $CO_2$. As indicated, all known prior art instruments have operated on the assumption that $CO_2$ absorbs infrared radiation of substantially all wavelengths in the region of 4.3 microns, and have consequently suffered from a fundamental inaccuracy. Empirical corrections made to adjust the readings of prior art instruments to match the concentrations of known samples are not satisfactory to compensate for this inevitable leakage.

A more accurate statement of Lambert's Law is thus as follows:

$$I = I_o L + I_o (1-L) e^{-abc}$$

where L is the light "leakage factor", i.e., the fraction of incident radiation not absorbed by $CO_2$. L is characteristic of the absorption spectrum of $CO_2$, or any other gas species of interest, by the cell of the particular instrument with respect to radiation from the lamp; L is responsive to the characteristics of the particular cell and interference filter chosen, as well as other windows or the like in the optical path.

L can be determined, and the instrument calibrated in order to correctly reflect leakage L inherent in the comb-like absorbtion spectrum of infrared radiation by any gas species of interest, in the following manner.

To calibrate the NDIR instrument of the invention, absorption measurements are made with samples of at least three different known concentrations. Preferably, one measurement is made at zero concentration and the remaining two measurements are representive of the scale used. For example, if the full-scale concentration range desired is 2000 ppm $CO_2$, one might choose 0 ppm, 200 ppm and 2000 ppm as the calibration points. Beginning with the basic response equation:

$$I = I_o L + I_o (1-L) e^{-abc}$$

we first measure, and note $I_0$. In the preferred single-cell embodiment, where $I_0$ is measured with reference to infrared-transparent nitrogen before each run, c becomes zero and I reduces to $I_o$ in the above equation. Next, we measure the transmission at the two additional concentration levels, expressing the measured percentage transmission of the nth run as $T_n$:

$$T_n = \frac{I_n}{I_0} = L + (1-L) e^{-abc}$$

In the preferred embodiment, in which the intensity I is measured as a number N indicative of the length of time required for the integrators to count down from an integrated total value to zero, and where $N_0$ is the value recorded with infrared-transparent nitrogen in the cell, the equation simply takes the form $$T_n = \frac{N}{N_0} = L + (1-L) e^{-abc}$$

From this equation we solve for the product ab for each run:

$$ab = \frac{\ln\left(\frac{1-L}{T_n - L}\right)}{c_n}$$

This product ab is the absorption coefficient of $CO_2$ times the path length and will remain constant at any concentration. Therefore, if we let $c_1$ be the concentration at 200 ppm and $c_2$ be the concentration at 2000 ppm, we can equate the two products ab as follows:

$$\frac{\ln\left(\frac{1-L}{T_1 - L}\right)}{c_1} = \frac{\ln\left(\frac{1-L}{T_2 - L}\right)}{c_2}$$

and solve iteratively for the light leakage factor L. The $CO_2$ concentration c corresponding to any measured value I can now be found using the original characteristic equation:

$$I = I_o L + I_o (1-L) e^{-abc}$$

It will be appreciated that the light leakage factor L provides a quantitative measure of the efficiency of the optical system, i.e., the lower L the better the system.

Conclusion

It will therefore be appreciated by those of skill in the art that there has been disclosed an NDIR instrument of unprecedented sophistication, particularly in that the existence of light leakage has been recognized by the inventor and Lambert's Law corrected accordingly. The dual-slope integrator circuitry provided allows superior signal-to-noise ratio, by allowing operation of the lamp at 1 Hz, while not unduly delaying the instrument's response. The cell design provides excellent temperature stability, further improving accuracy. Electronic modulation of the lamp between low and high current levels of reversed polarity improves lamp life and eliminates any need for a mechanical chopper.

As discussed above, the instrument of the invention may be provided in single- and dual-beam embodiments. Each has advantages and disadvantages. The single-beam device has the advantage that detector-induced noise is reduced to a minimum; the optimal accuracy of measurement is realized in this embodiment of the invention. However, this embodiment requires periodic "blanking" using an infrared-transparent gas, complicating the installation of the instrument, and the instrument is subject to long-term drift. By comparison, the dual-beam instrument, employing a second detector in a servo loop to control the lamp intensity to a constant value, is relatively immune to long-term drift, although use of the second detector increases noise in the instrument.

More specifically, in applications wherein a nitrogen gas stream is available for regular, automatic calibration, slowly changing drift due to lamp aging is not consequential and the performance limitation is noise. Because the noise floor is due to thermal noise in the pyroelectric detector, the use of a single pyroelectric detector in a single beam embodiment of the invention gives the best performance. In applications wherein calibrations are performed infrequently, drift due to lamp aging generally becomes larger than the thermal noise. In these circumstances, a dual-beam embodiment, comprising an additional pyroelectric detector in a servo loop to stabilize the lamp output, becomes advantageous.

While a preferred and several alternative embodiments of this invention have been disclosed herein, the invention should not be limited thereby, but only by the following claims.

What is claimed is:

1. An instrument for non-dispersive infrared (NDIR) measurement of the concentration of an infrared-absorptive gas species in a gas sample, comprising:

an elongated sample cell having an inlet and an outlet, and infrared-transparent windows at opposed ends of said cell;

an infrared-emitting lamp juxtaposed to the outer surface of the window at a first end of said cell;

a first pyroelectric detector juxtaposed to the outer surface of the window disposed at the opposed end of said cell;

means for supplying a square wave drive signal of controllable amplitude to said lamp;

means for processing a signal provided by said pyroelectric detector responsive to the intensity of infrared radiation from said lamp incident thereon, to yield an output signal proportional to the infrared absorptivity of a gas sample in said cell; and means for determining the concentration of the infrared-absorptive gas species in said cell responsive to said output signal, said means for determining compensating said output signal responsive to a leakage factor L, characteristic of the absorption spectrum of the gas species within the cell with respect to radiation from said lamp.

2. The instrument of claim 1, wherein the leakage factor L is determined by measurement of the intensity of radiation incident on said detector with respect to plural calibration samples of known concentrations of the absorbent gas.

3. The instrument of claim 2, wherein the leakage factor L is determined by iterative solution of $$\frac{\ln\left(\frac{1-L}{T_1-L}\right)}{c_1} = \frac{\ln\left(\frac{1-L}{T_2-L}\right)}{c_2}$$

where $C_1$ and $C_2$ are known values of the percentage concentration of the absorbent gas; and $T_1$ and $T_2$ are measured values of the percentage of transmission of radiation through the corresponding samples.

4. The instrument of claim 1, wherein said means for supplying a square wave drive signal to said lamp modulates the lamp drive signal between high and low levels.

5. The instrument of claim 4, wherein said means for supplying a square wave drive signal to said lamp alternates the polarity of said lamp drive signal on alternate cycles.

6. The instrument of claim 1, wherein said signal provided by said first pyroelectric detector is an AC signal, and said means for processing said signal provided by said first pyroelectric detector comprises means for inverting the AC input signal, means for supplying the input signal and the inverted input signal each to one of a pair of dual-slope integrators each integrating the positive half-cycles of the corresponding signals, and means for processing successive integrated values of each positive half-cycle of the input signal and the inverted input signal to yield a value for the amount of radiation incident on said detector during each half-cycle.

7. The instrument of claim 6, wherein said dual-slope integrators each comprise capacitors charged at a rate responsive to the instantaneous amplitude of the signal supplied thereto during the positive half-cycle thereof, and discharged at a constant rate during the negative half-cycle thereof.

8. The instrument of claim 7, wherein said integrated values of each half-cycle of the AC signal are determined by measuring the time required for said capacitors to discharge at said constant rate during the negative half-cycle of the corresponding input signal.

9. The instrument of claim 6, wherein each said integrator comprises switching means operated in synchronism with the zero-crossings of the input signal for controlling the transition between charging and discharging said capacitors.

10. The instrument of claim 9, wherein said switching means is operated responsive to a control signal synchronized to transitions in said square-wave lamp drive signal.

11. The instrument of claim 10, wherein said control signal is provided by a timer provided by a timer also controlling said square-wave lamp drive signal, such that said operation of said switching means is delayed with respect to said transitions in said square-wave lamp drive signal by a phase lag $\phi$.

12. The instrument of claim 11, wherein said phase lag $\phi$ is determined at start-up of operation of said instrument by comparing zero-crossings of said AC input signal provided by said first pyroelectric detector to said transitions in said square-wave lamp drive signal.

13. The instrument of claim 1, further comprising means for determining a phase lag $\phi$ between transitions of said lamp drive signal and zero-crossings of an AC input signal provided by said first pyroelectric detector, and means for providing a control signal to switching means for rectifying the output signal provided by said first pyroelectric detector, said control signal being phase-delayed with respect to said lamp drive signal by said phase lag $\phi$.

14. The instrument of claim 1, wherein said sample cell is of a highly heat-conducting material, said pyroelectric detector is mounted in good heat-conducting relation with said cell, and means are provided for regulating the temperature of the assembly of said cell and said detector constant.

15. The instrument of claim 14, wherein said means for regulating the temperature of the assembly of said sample cell and of said pyroelectric detectors constant comprises one or more heater servo circuits, each comprising a thermistor for measuring temperature, and a heating element for heating said assembly responsive to the output of said thermistor.

16. The instrument of claim 15, wherein said servo circuit further comprises a phase compensation network allowing said heating element to be driven at high gain with respect to the signal provided by said thermistor.

17. The instrument of claim 16, wherein said heating element is a power transistor in thermal contact with said assembly.

18. The instrument of claim 17, wherein two identical heater servo circuits are provided, the power transistor of each being in direct thermal contact with metallic housings defining opposite ends of said cell.

19. The instrument of claim 18, further comprising a second pyroelectric detector disposed behind said lamp at said first end of said cell, an output signal from said second detector being employed in a servo loop to maintain the output of infrared radiation from said lamp constant over time.

20. The instrument of claim 19, wherein said lamp is disposed within a sealed chamber interposed between said window at said first end of said cell and a similar window juxtaposed to said second pyroelectric detector.

21. The instrument of claim 19, wherein said square wave lamp drive signal varies between a "high" current level and a non-zero "low" current level, and wherein said servo loop controls the high current level of said square wave lamp drive signal such that the output signal from said second detector is maintained at a constant amplitude during said "high" portions of said lamp drive signal.

22. In combination, the instrument of claim 1 with a source of blanking gas of known composition not absorptive of infrared radiation, a valve controlling alternating connection of the inlet of said cell to said source of blanking gas and the source of said gas sample, and means for comparing signals measured by said first pyroelectric detector at a time said cell is filled with blanking gas to similar signals measured at a time said cell is filled with said gas sample.

23. A method for non-dispersive infrared (NDIR) measurement of the concentration of an infrared-absorptive gas sample, comprising the steps of:

providing a cell having an inlet and an outlet, an infrared-emitting lamp juxtaposed to an infrared-transparent window at one extremity of said cell and a first pyroelectric detector juxtaposed to a similar window at an opposed extremity of said cell, supplying a square wave drive signal to said lamp, said drive signal being controlled to ensure that the intensity of radiation provided by said lamp remains constant, processing a signal provided by said first pyroelectric detector responsive to the intensity of infrared radiation from said lamp incident thereon, to yield an output signal proportional to the infrared absorptivity of a gas sample in said cell; and determining the concentration of an infrared-absorptive gas species in said cell responsive to said output signal, said determining step including the step of compensating the output signal from the detector responsive to calibration measurements of a leakage factor L, said factor L being characteristic of the absorption spectrum of the gas species within the cell with respect to radiation from said lamp.

24. The method of claim 23, wherein the leakage factor L is determined by measurement of the intensity of radiation incident on said detector with respect to plural calibration samples of known concentrations of the absorbent gas.

25. The method of claim 24, wherein the leakage factor L is determined by iterative solution of $$\frac{\ln\left(\frac{1-L}{T_1-L}\right)}{c_1} = \frac{\ln\left(\frac{1-L}{T_2-L}\right)}{c_2}$$

where $C_1$ and $C_2$ are known values of the concentration of the absorbent gas; and $T_1$ and $T_2$ are the measured values of the transmission of radiation through the corresponding samples.

26. The method of claim 24, wherein said step of supplying a square wave drive signal to said lamp, said drive signal being controlled to ensure that the intensity of radiation provided by said lamp remains constant, is performed by measuring the intensity of radiation emitted by said lamp, and controlling the amplitude of said lamp drive signal accordingly.

27. The method of claim 26, wherein said instrument is operated in combination with a source of purge gas of known composition not absorptive of infrared radiation, and said step of measuring the intensity of radiation emitted by said lamp is performed by measuring said output signal with said cell filled with purge gas.

28. The method of claim 26, wherein said step of measuring the intensity of radiation emitted by said lamp is performed employing a second pyroelectric detector disposed on a side of said lamp away from said cell and operated in a servo loop operated to ensure that the intensity of radiation incident on said second pyroelectric detector is maintained constant over time.

29. The method of claim 26, wherein said square wave lamp drive signal varies between a "high" current level and a non-zero "low" current level, and wherein said servo loop controls the high current level of said square wave lamp drive signal such that the output signal from said second detector is maintained at a constant amplitude during said "high" portions of said lamp drive signal.

30. The method of claim 23, wherein said signal provided by said first pyroelectric detector responsive to the intensity of infrared radiation from said lamp incident thereon is an AC signal, said AC signal being integrated on alternate half-cycles thereof in order to provide a series of values each proportional to the infrared absorptivity of a gas sample in said cell.

31. The method of claim 30, wherein said step of integration comprises the step of dual-slope integration performed separately with respect to alternating half-cycles of said AC output signal.

32. The method of claim 31, wherein two separate dual-slope integrators are provided, the AC input signal being applied directly to one, and the AC input signal being inverted and applied to the other, said dual-slope integrators each comprising capacitors charged at a rate responsive to the instantaneous amplitude of the input signal supplied thereto during the positive half-cycle thereof, and discharged at a constant rate during the negative half-cycle thereof.

33. The method of claim 32, comprising the step of determining said integrated values of each half-cycle of the AC signal by measuring the time required for said capacitors to discharge at a constant rate during the negative half-cycle of the corresponding input signal.

34. The method of claim 23, comprising the step of controlling the transition between charging and discharging said capacitors responsive to a control signal provided by a timer also controlling transitions in said square-wave lamp drive signal.

35. The method of claim 34, wherein said control signal provided by said timer is delayed with respect to said transitions in said square-wave lamp drive signal by a phase lag $\phi$, and further comprising the step of determining said phase lag $\phi$ at start-up of operation of said instrument by comparing zero-crossings of said AC input signal provided by said first pyroelectric detector to said transitions in said square-wave lamp drive signal.

36. An instrument for non-dispersive infrared measurement of the infrared absorptivity of a gas sample, comprising:

a sample cell of a highly heat-conducting material, defining a sample volume and having an inlet and an outlet, and infrared-transparent windows at opposed ends of said cell;

an infrared-emitting lamp juxtaposed to the outer surface of the window at a first end of said cell;

a first pyroelectric detector juxtaposed to the outer surface of the window at the opposed end of said cell;

said pyroelectric detector being mounted in good heat-conducting relation with said cell; and one or more heater servo circuits, each servo circuit comprising a thermistor for measuring temperature of the assembly of said cell and said detector and a power transistor in thermal contact with said assembly for serving as a heating element for heating said assembly responsive to the output of said thermistor, for regulating the temperature of the assembly of said cell and said detector constant.

37. The instrument of claim 36, wherein said pyroelectric detector and said heating elements are connected directly to a circuit board to which are also mounted components of signal amplification and processing circuitry.

38. The instrument of claim 36, further comprising a second pyroelectric detector, disposed on a side of said lamp away from said cell and providing a second output signal responsive to the intensity of radiation incident on said second pyroelectric detector, and servo loop circuit means responsive to said second output signal for controlling means for supplying a square wave lamp drive signal of controllable amplitude to said lamp.

39. The instrument of claim 38, wherein said servo loop circuit means controls the high level of said square wave lamp drive signal responsive to said second output signal, the low level thereof being maintained at a fixed non-zero reference value.

40. The instrument of claim 38, wherein two substantially identical heater servo circuits are provided, the power transistor of each being in direct thermal contact with metallic housings in which said detectors are disposed, said housings further being in good heat-conducting relation with said sample cell.

41. The instrument of claim 39, wherein said lamp is disposed within a sealed chamber interposed between said window at said first end of said cell and a similar window juxtaposed to said second pyroelectric detector.

42. The instrument of claim 41, wherein said sealed chamber within which said lamp is disposed is formed within a block of highly heat-conductive material in thermal contact with said cell and the housing of said second pyroelectric detector.

43. A method for non-dispersive infrared measurement of the infrared absorptivity of a gas sample, comprising the steps of:

providing an instrument comprising:
a sample cell defining a sample volume and having an inlet and an outlet, and infrared-transparent windows at opposed ends of said cell;
an infrared-emitting source juxtaposed to the window at a first end of said cell;
a first pyroelectric detector disposed at the opposed end of said cell;
a second pyroelectric detector disposed on a side of said source away from said cell;
means for modulating the intensity of radiation incident on said first and second detectors from said source between high and low levels, at regular intervals; and
a power supply connected in a servo loop including said source and said second pyroelectric detector, for maintaining the intensity of radiation incident on said second pyroelectric detector constant during the time said radiation is incident thereon at said high level;

admitting a gas sample to be tested to the sample volume defined by said cell;

processing an AC output signal provided by the first pyroelectric detector to yield a signal indicative of the intensity of radiation incident thereon.

44. The method of claim 43, wherein the intensity of radiation from said source is modulated between high and low levels at regular intervals by supplying a square wave drive signal to said source.

45. The method of claim 44, wherein said servo loop including said second pyroelectric detector controls the amplitude of a square wave drive signal supplied to said source such that the intensity of radiation provided by said source during high portions of said square wave drive signal remains constant, by measuring the intensity of radiation emitted by said source, and controlling the amplitude of said drive signal accordingly.

46. The method of claim 43, wherein said step of processing an AC output signal provided by the first pyroelectric detector to yield a signal indicative of the intensity of radiation incident thereon is performed by integrating alternate half-cycles of the input AC signal to yield a series of values for the intensity of radiation incident on said first detector.

47. The method of claim 46, wherein two separate integrators are provided, the input AC signal being applied to one and an inverted input AC signal to the other, each integrator being storing values responsive to the instantaneous amplitude of the AC input signal supplied thereto during the positive half-cycle of the AC input signal, the total thus integrated being measured after completion of the positive half-cycle thereof.

48. The method of claim 47, wherein said integrators are dual slope integrators, each comprising capacitors storing charge at a rate responsive to the rate of change of temperature of the first pyroelectric detector during the positive half-cycle of the AC input signal, and wherein said stored values are measured by measuring the time required for said capacitors to discharge at a constant rate during the negative half-cycle of the corresponding input signal.

49. The method of claim 48, wherein said time is measured using a digital timer, whereby a series of digital values for the intensity of radiation incident on the detector during successive half-cycles of the input signal is provided.

50. The method of claim 49, comprising the step of controlling the transition between integrating said input signal and measuring the integrated value thereof responsive to a control signal provided by a timer also controlling transitions in said modulated source intensity.

51. The method of claim 50, wherein said control signal provided by said timer is delayed with respect to said transitions in said modulated source intensity by a phase lag $\phi$, and comprising the step of determining said phase lag $\phi$ at start-up of operation of said instrument, by comparing zero-crossings of said AC input signal provided by said first pyroelectric detector to said transitions in said modulated lamp intensity.

52. The method of claim 43, comprising the further step of determining the concentration of an infrared-absorptive gas species in said cell responsive to said output signal, said determining step including the step of compensating the DC output signal from the detector responsive to calibration measurements of a leakage factor L, said factor L being characteristic of the absorption spectrum of the gas species within the cell with respect to radiation from said lamp.

53. The method of claim 52, wherein the leakage factor L is determined by measurement of the intensity of radiation incident on said detector with respect to plural calibration samples of known concentrations of the absorbent gas.

54. The method of claim 53, wherein the leakage factor L is determined by iterative solution of $$\frac{\ln\left(\frac{1-L}{T_1-L}\right)}{c_1} = \frac{\ln\left(\frac{1-L}{T_2-L}\right)}{c_2}$$

where
$C_1$ and $C_2$ are known values of the concentration of the absorbent gas; and
$T_1$ and $T_2$ are the measured values of the transmission of radiation through the corresponding samples.

* * * * *